(12) United States Patent
Fontana

(10) Patent No.: US 6,211,239 B1
(45) Date of Patent: Apr. 3, 2001

(54) METHOD FOR TREATING OR PREVENTING BREAST CANCER OR LEUKEMIA USING 6-[3-[1-ADAMANTYL]-4-HYDROXYPHENYL]-2-NAPHTHALENE CARBOXYLIC ACID (AHPN)

(75) Inventor: Joseph A. Fontana, Ellicott City, MD (US)

(73) Assignee: Centre International de Recherches Dermatologiques Galderma, Valbonne (FR)

( * ) Notice: Subject to any disclaimer, the term of this patent is extended or adjusted under 35 U.S.C. 154(b) by 0 days.

(21) Appl. No.: 09/011,323

(22) PCT Filed: Jul. 17, 1996

(86) PCT No.: PCT/US96/11736

§ 371 Date: Jun. 29, 1998

§ 102(e) Date: Jun. 29, 1998

(87) PCT Pub. No.: WO97/03682

PCT Pub. Date: Feb. 6, 1997

(51) Int. Cl.$^7$ .................................................. A61K 31/19
(52) U.S. Cl. ............................................................ 514/569
(58) Field of Search ............................................... 514/569

(56) References Cited

U.S. PATENT DOCUMENTS 4,717,720   1/1988   Shroot et al. ........................ 514/56

*Primary Examiner*—Jerome D. Goldberg
(74) *Attorney, Agent, or Firm*—Burns, Doane, Swecker & Mathis, L.L.P.

(57) ABSTRACT

Methods for treating or preventing breast cancer or leukemia in subjects in need of such treatment are provided which involve the administration of 6-[3-[1-adamantyl]-4-hydroxyphenyl]-2-naphthalene carboxylic acid (AHPN), a retinoid which induces $G_0/G_1$ arrest and apoptosis. These methods are useful for treatment of breast cancers which express or do not express estrogen receptors.

4 Claims, 10 Drawing Sheets

Figure 1:
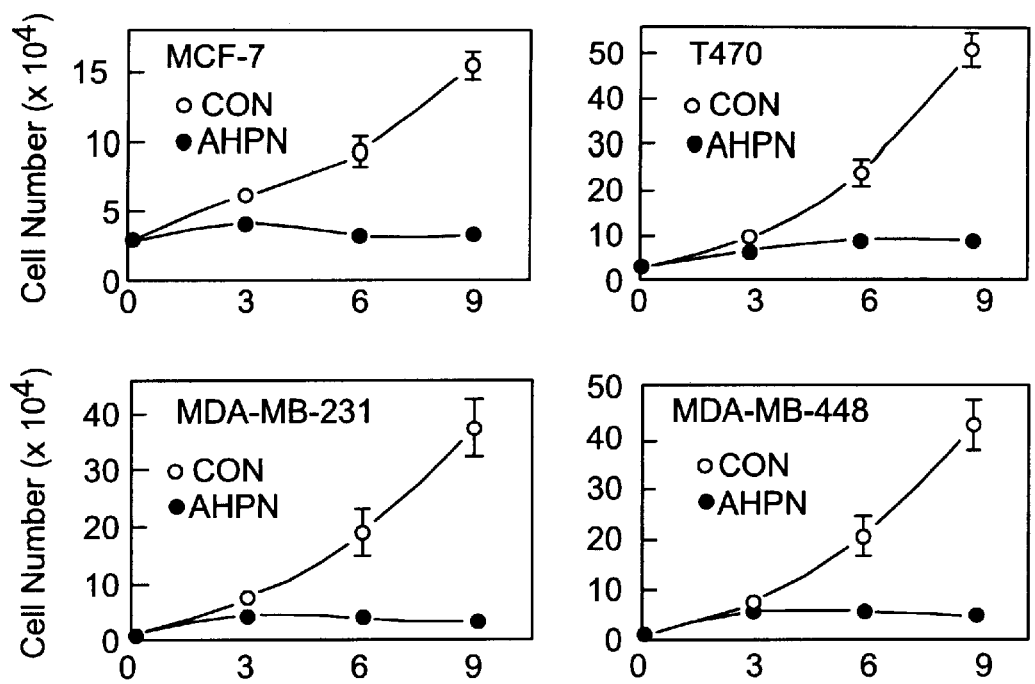

METHOD FOR TREATING OR PREVENTING BREAST CANCER OR LEUKEMIA USING 6-[3-[1-ADAMANTYL]-4-HYDROXYPHENYL]-2-NAPHTHALENE CARBOXYLIC ACID (AHPN)

FIELD OF THE INVENTION

The present invention relates to the use of a retinoid having unique properties for the treatment or prevention of breast cancer or leukemia. More specifically, the present invention relates to the use of 6-[3-[1adamantyl]-4-hydroxyphenyl]-2-naphthalene carboxylic acid (AHPN) to treat or prevent breast cancer or leukemia.

BACKGROUND OF THE INVENTION

Retinoids are defined as substances that can elicit specific biological responses by binding to and activating a specific receptor or set of receptors. Retinoids are known to play a fundamental role in normal cell growth and differentiation. (Roberts, A. B. et al, in "The Retinoids," ed. by M. B. Sporn, A. B. Roberts and D. S. Goodman, Vol. 2, pp. 209–256, Academic Press, Orlando, Fla., (1984); Sporn, M. B. et al, *J. Amer. Acad. Dermatol.,* 15:756–764 (1986)). Multiple retinoic acid nuclear receptors. (RARα, β and γ) and retinoid X receptors (RXRα, β and γ) have been identified (Evans, R. M., *Science,* 240:889–895 (1988); O'Malley, B. W., *Mol. Endocrin.,* 4:363–364 (1990); Gudas, L. J. *Cell Growth Differ,* 3:655–662 (1992)); Lohnes et al, *Cell Sci.,* 16 (Suppl): 69–76 (1992). Moreover, numerous isoforms of the various nuclear receptors exist as a result of alternative splicing (Gudas L. J., *J. Biol. Chem.,* 269:15399–15402 (1994)).

Retinoic acid receptors mediate gene transcription through a variety of mechanisms. These nuclear receptors can bind to specific DNA consensus sequences termed retinoid receptor response elements (RAREs or RXREs) which are located in the regulatory regions of the retinoid target genes (Gudas, L. J., *Cell Growth Differ.,* 3:655–662 (1992); Lohnes et al, *Cell Sci.,* 16 (Suppl.):69–76 (1992)). Nuclear receptor binding to these response elements preferably occurs through heterodimer formation between the RAR and RXR, although homodimer binding and subsequent gene activation has also been found (Hermann et al, *Mol. Endocrinol.,* 6:1153–1162 (1992); Leid et al, *Cell,* 68:377–395 (1992); Zhang X, *Nature,* 355:441–446 (1992)). The RXRs can mediate gene transcription via heterodimer formation with the RARs, with the vitamin D, thyroid hormone (Yu et al, *Cell,* 67:1251–1266 (1991); Hermann et al, *Mol. Endocrinol.,* 6:1153–1162 (1992); Kliewer et al, *Nature,* 355:446–449 (1992); Leid et al, *Cell,* 68:377–395 (1992); Zhang et al, *Nature,* 355:441–446 (1992)), and a number of orphan receptors. (Apfel et al, *Mol. Cell Biol.,* 14:7025–7035 (1994); Song et al, *Proc. Natl. Acad. Sci., USA* 91:10809–10813 (1994)). These orphan receptors can, in turn, inhibit the activity of RARs and thyroid nuclear receptors (TRs) (Kliewer et al, *Proc. Natl. Acad. Sci., USA,* 89:1448–1452 (1992); Tran et al, *Mol. Cell Biol.,* 12:4666–4676 (1992); Apfel et al, *Mol. Cell Biol.,* 14:7025–7035 (1994), Casanova et al, *Mol. Cell Biol.,* 14:5756–5765 (1991); Song et al, *Proc. Natl. Acad. Sci., USA,* 91:10809–10813 (1994)).

The retinoid receptor response elements usually consist of direct repeats (DRs) in which the half-sites are separated by a number of base pair spacers. Selectivity for binding appears to be determined by the number of base pairs utilized as spacers, as well as by the sequence of the response element itself (Kim et al, *Mol. Endocrinol.,* 6:1489–1501 (1992), Mader et al, *J. Biol. Chem.,* 268:591–600 (1993)).

RAR and RXR inhibition of AP-1-mediated gene transcription that does not require RAR or RXR binding to DNA has also been observed (Pfahl, *Endocrin. Reviews,* 14:651–658 (1993), and references cited therein); RAR and RXR when completed to their ligands have been shown to inhibit c-Jun/c-Fos binding to the AP-1 consensus sequence and subsequent gene activation (Pfahl, *Endocrine Reviews,* 14:651–658 (1993), and references cited therein). Negative regulation of transcription by RA can apparently also occur by means that do not involve RAR binding to the promoter region but by inhibiting enhancer activity (Gudas, *J. Biol. Chem.,* 269:15399–15402 (1994)). In addition, negative regulation of RAR-mediated, as well as TR-mediated, gene transcription occurs by the competitive binding of the orphan receptor coup and v-ErbA to RARE and TREs (Tran et al, *Mol. Cell. Biol.,* 12:4666–4676 (1992), Hermann et al, *Oncogene,* 8:55–65 (1993)).

Most cell types express more than one RAR and RXR receptor. RAR homologous recombination studies have suggested that RAR functional redundancy exists among the different RARs (Li et al, *Proc. Natl. Acad. Sci., USA,* 90:1590–1594 (1993), Lohnes et al, *Cell,* 73: 643–658 (1993), Lufkin et al, *Proc. Natl. Acad. Sci., USA,* 90:7225–7229 (1993)). However, other studies have indicated that the various receptor subtypes possess distinct functions and may indeed modulate the activity of distinct genes (Nagpal et al, *Cell,* 70:1007–1019 (1992); Boylan et al, *Mol. Cell Biol.,* 15:843–851 (1995)). Evidence also suggests a unique role for each of the receptor subtypes: (1) receptor selectivity towards specific transactivating response elements has been demonstrated (Nagpal et al, *Cell,* 70:1007–1019 (1992)); and (2) specific cell types have become refractory to the antiproliferative and differentiating effects of RA with the loss of one receptor subtype, despite the presence of other RAR subtypes (Sheikh et al, *J. Cell Biochem.,* 53:393–403 (1993); Moasser et al, *Oncogene,* 9:833–840 (1994)).

The RARs bind both RA and its isomer 9-cis-RA, while the RXRs only bind 9-cis-RA (Allenby et al, *J. Biol. Chem.,* 269:16689–16695 (1995), and references cited therein). To further document a unique function for each receptor subtype, conformationally restricted retinoids have been synthesized that selectively bind to and enhance transcriptional activation by selective RAR and RXR subtypes (Graupner et al, *Biochem. Biophys. Res. Commun.,* 179:1554–1561 (1991); Lehmann et al, *Cancer Res.,* 61:4804–4809 (1991), Lehmann et al, *Science,* 258:1944–1946 (1992); Dawson et al, in "Retinoids: New Treatments in Research and Clinical Applications". Livrea M A and Packer L., (eds) Marcel Dekker: NY pp 205–221 (1992); Davies et al, *Amer. Ass'n of Cancer Res. Conf.,* Banff, Alberta, Canada, Mar. 15–20 (1993) Abst. B-28; Jong et al, *J. Med. Chem.,* 36:2605–2613 (1993); Reichert et al, from "Mol. Biol. to Therapeutics: Pharmacology of the Skin", Vol. 5, Bernard B A and Shroot B (eds), Karger: B.2d pp 117–127 (1993); Beard et al, *Bioorg. Med. Chemical,* 4:1447–1452 (1994); and Boehm et al, *J. Med. Chem.,* 37:2936–2941 (1994)).

These synthetic receptor-selective retinoids have further confirmed the uniqueness of specific RAR sub-types in modulating RA responses in various cell types (Rudd et al, *Cancer Letter,* 73:41–49 (1993); Sheikh et al, *J. Biol. Chem.,* 269:21440–21447 (1994)). Recently, a series of synthetic retinoids has been described that selectively transactivate RARγ (Bernard et al, *Biochem. Biophys. Res. Comm.*, 186 (2):977–983 (1992)).

Because of the ability of retinoids to affect cell growth and differentiation, these compounds have been disclosed to be useful for the treatment or prevention of diseases and conditions involving abnormal cell proliferation and differentiation. For example, the usage of retinoids as efficient therapeutics for the treatment of various skin diseases and neoplasms has been reported (Roberts, A. B. and Sporn, M. B., in "The Retinoids", Sporn et al, pp 209–286, Academic Press, Orlando, Fla; Bollag et al, *Ann. Oncol.*, 3:513–526 (1992); Smith et al, *J. Clin. Oncol.*, 10:839–864 (1992)).

To date, the best results of retinoid therapy have typically been achieved with a regimen which combines retinoid administration with the administration of other differentiation or cytotoxic agents. Besides retinol and retinoic acid, isotretoin (13-cis-retinoic acid) and etretinate have been used, as well as 9-cis retinoic acid and N-(9-hydroxyphenyl) retinoid.

The most convincing results have been documented in the field of dermological disorders, where topical application can circumvent the toxic effects sometimes observed during systemic administration of retinoids. For example, retinoids have been reported to be useful for the treatment of a variety of dermatoses including psoriasis, cystic acne, cutaneous disorders of keratinazation, among others.

Besides dermatological disorders, retinoids have important potential as anti-cancer agents. For example, retinoid compounds have been disclosed to have potential for the prevention of skin cancer, for the treatment of acute myeloid leukemia (AML), acute promyelocytic leukemia (APL) for the treatment of other hematopoietic malignancies such as myelodysplastic syndrome, juvenile chronic myelogenous leukemia, Sezary syndrome, squamous cell carcinomas of the upper aerodigestive tract, non-small lung cancer, and human head and neck carcinomas. (See Pfahl et al, *Vitamins and Hormones*, 49:327–382 (1993) at 363–366, which reviews the usage of retinoids as therapeutics).

In the specific case of breast cancer, the growth of some breast cancer cell lines has been reported to be inhibited by retinoids (La Croix et al, *J. Clin. Invest.*, 65:586–591 (1980)). Also, etretinate has been reported to prevent the growth of xenotransplanted breast carcinoma cells in athymic mice (Halter et al, *Cancer Res.*, 48:3733–3736 (1988)). Further, it has been reported that N-(4-hydroxyphenyl) retinamide (4-HPR) induces apoptosis and the differentiation of breast cancer cell lines, assertedly independent of the status of estrogen receptor (ER) and RAR expression (Pellegrini et al, *Cell Growth Differ.*, 6(7):863–869 (1995)).

Also, a recent patent issued to Curley et al, U.S. Pat. No. 5,516,792, assigned to Ohio State Research Foundation, teaches the use of retinoyl beta-glucuronide N-glycoside analogs for the treatment, prevention and study of cancers, including breast cancer. Further, N-(4-hydroxyphenyl) retinamide (4-HPR), a derivative of trans-retinoic acid, is currently in clinical trials as a chemopreventive agent for breast cancer.

Additionally, retinoic acid in combination with RAR-β receptors has been reported to promote apoptosis of estrogen receptor-positive (ER+) human breast cancer cell lines (Liu et al, *Mol. Cell Biol.* 16(3):1138–1149 (1996)).

Further, the use of retinoic acid in combination with interferon, specifically alpha interferon or gamma interferon, has been reported to inhibit the proliferation of some breast cancer cell lines (Widschwendter et al, *Anticancer Res.*, 16 (1):369–374 (1996); Widschwendter et al, *Cancer Res.*, 55(10):2135–2139 (1995)).

Also, 9-cis retinoic acid has been reported to inhibit the growth of breast cancer cells and to down-regulate estrogen receptor RNA and protein (Rubin et al, *Cancer Res.*, 54(24) :6549–6556 (1994)).

Still further, the use of (4-HPR) in combination with the anti-estrogen tamoxifen as a potential synergistic combination for breast cancer chemoprevention has been reported (Costa, A., *Eur. J. Cancer*, 29A(4):589–592 (1993)).

However, while some retinoids have been reported to have potential as anticancer agents, and specifically for the treatment or prevention of breast cancer and leukemia, the identification of retinoids having improved therapeutic properties which are suitable for the treatment or prevention of such cancers would be highly beneficial. In particular, the identification of retinoids which are cytotoxic to either estrogen receptor positive or estrogen receptor negative breast cancers would be highly beneficial.

OBJECTS AND BRIEF DESCRIPTION OF THE INVENTION

It is an object of the invention to provide a novel method for the treatment or prevention of breast cancer or leukemia, involving the administration of a retinoid which induces $G_0/G_1$ arrest and apoptosis.

It is a more specific object of the invention to provide a novel method for treating or preventing breast cancer or leukemia involving the administration of a therapeutically or prophylactically effective amount of 6-[3-adamantyl-4-hydroxypropyl]-2-naphthalene carboxylic acid to a subject in need of such treatment or prevention.

It is a more specific object of the invention to provide a novel method for treating or preventing breast cancer involving the administration of a therapeutically or prophylactically effective amount of 6-[3-adamantyl4-hydroxypropyl]-2-naphthalene carboxylic acid to a subject in need of such treatment or prevention.

It is another object of the invention to provide a novel composition adopted for the treatment or prevention of breast cancer or leukemia which comprises a therapeutically or prophylactically effective amount of 6-[3-adamantyl-4-hydroxyphenyl]-2-naphthalene carboxylic acid.

Thus, the subject invention essentially relates to the usage of a specific retinoid, 6-[3-adamantyl-4-hydroxyphenyl]-2-naphthalene carboxylic acid which induces $G_0/G_1$ arrest and apoptosis for the treatment or prevention of breast cancer or leukemia, as well as pharmaceutical compositions adopted for the treatment or prevention of breast cancer or leukemia which contain an effective amount of 6-[3-adamantyl-4-hydroxyphenyl]-2naphthalene carboxylic acid.

DETAILED DESCRIPTION OF THE FIGURES

FIG. 1 shows the inhibition of breast carcinoma cell proliferation by AHPN. The tested breast carcinoma cell lines were seeded at a cell concentration of 3×10 or 1×10$^4$ cells per well in DMEM:F-12 medium supplemented with 5% FBS. The cells were then incubated overnight at which time AHPN was added to a final concentration of 1 μm. The data in the figure represents the mean ±SEM of three different experiments.

Figure 2:
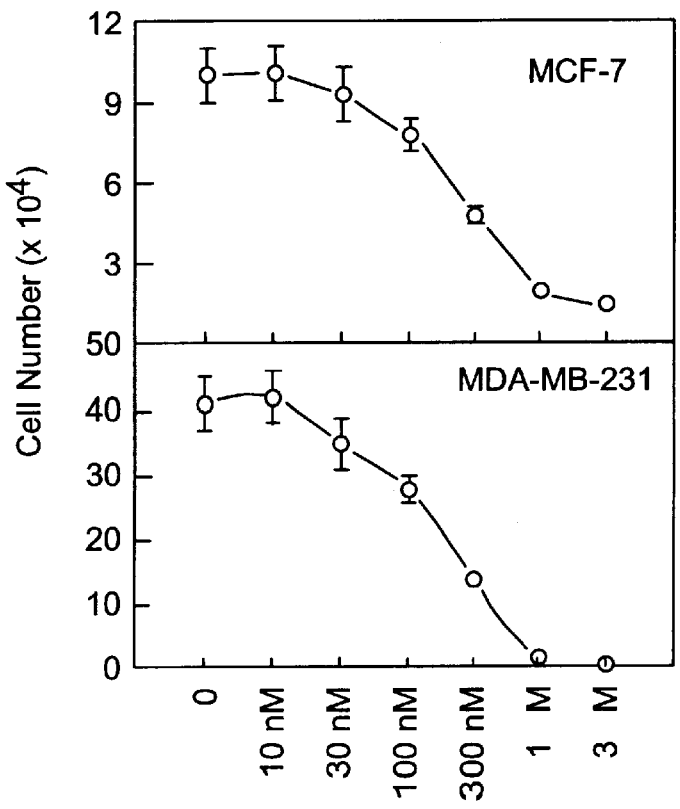

FIG. 2 shows the effects of varying the concentration of AHPN on MCF-7 and MDA-MB-231 proliferation. MCF-7 cells and MDA-MB-231 cells were seeded in DMEM:F-12 supplemented with 5% FBS in 24-well plates at a cell concentration of 3×10$^4$ and 1×10$^4$ cells, respectively, per well. The cells were incubated for 24 hours at which time varying concentrations of AHPN were added. Control cells were treated with vehicle alone. The medium and AHPN were changed every 2 days and cells in triplicate wells were counted after a 6 day incubation period. The data represent the mean ±SEM of three independent experiments.

Figure 3A:
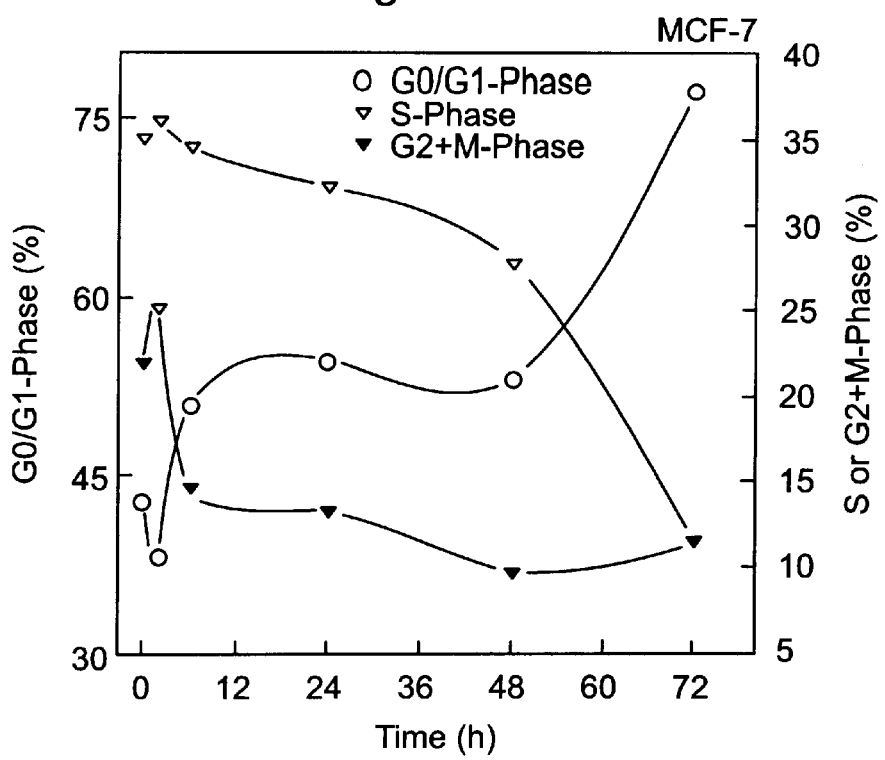
Figure 3B:
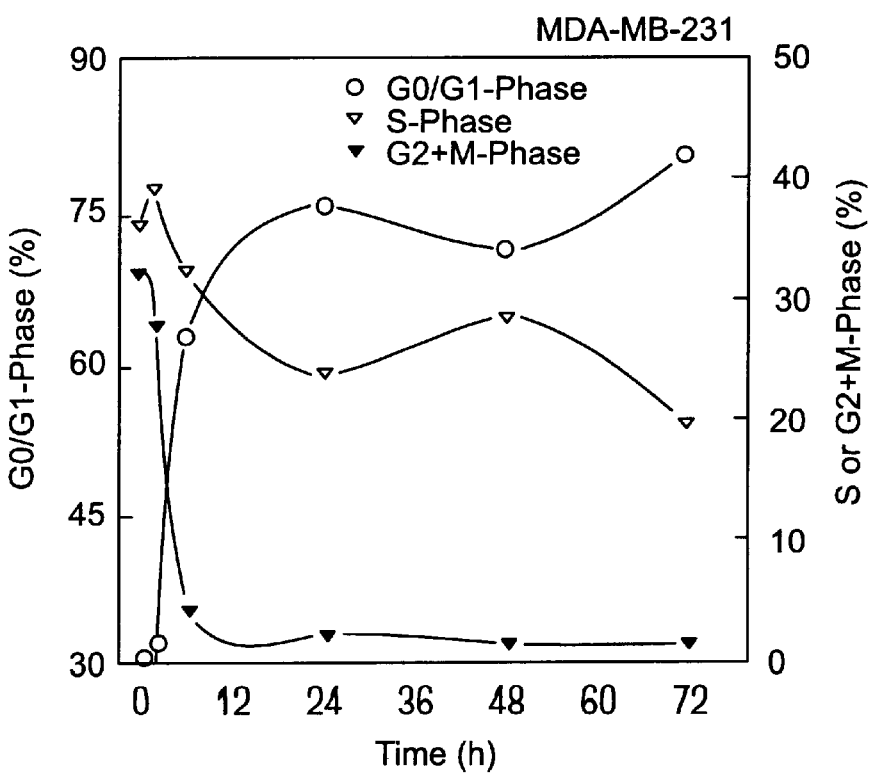

FIGS. 3A and 3B, respectively, show $G_1$ arrest of MCF-7 and MDA-MB-231 cells by AHPN. AHPN was added to a final concentration of 1 μM to MCF-7 and MDA-MB-231 cells logarithmically growing in DMEM:F-12 supplemented with 5% FBS. Cells were harvested at various times, the DNA stained with propidium iodide and the cell cycle phase distribution then determined.

Figure 4A:
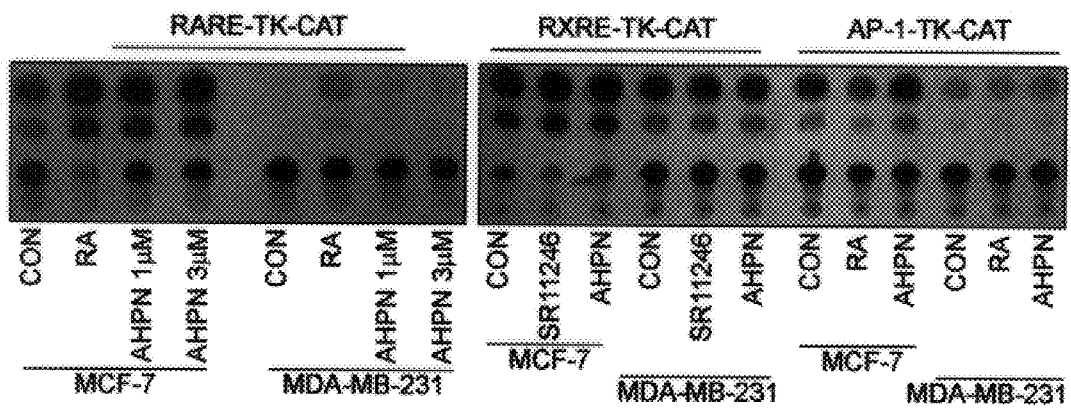
Figure 4B:
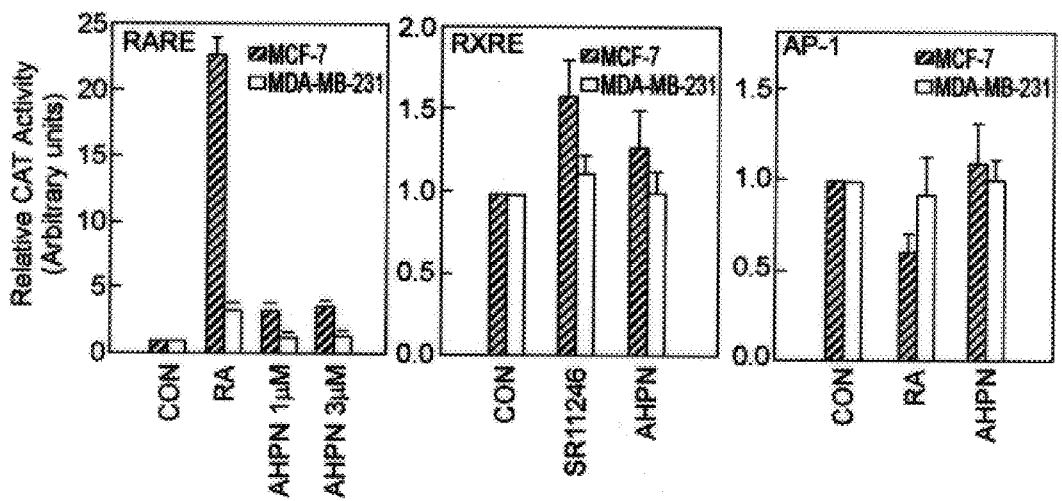

FIGS. 4A and 4B compare AHPN- and RA-mediated RARE and RXRE transactivation and anti-AP-1 activity in MCF-7 and MDA-MB-231 cells. MDA-MB-231 and MCF-7 cells logarithmically growing in 10 cm plates (approximately $3 \times 10^6$ cells per plate) in regular medium were transiently transfected with the indicated plasmid and treated with either 1 μM RA or 1 μM AHPN for 48 hours. CAT assays were then effected to measure gene expression. Also, $^{14}C$-activity was quantified by laser densitometry. Activation is expressed as the ratio of converted $^{14}C$ activity in the diacetate and monoacetate forms to the total $^{14}C$ activity. FIG. 4A shows the results of a representative CAT assay and FIG. 4B is the quantification of two different experiments. The values are expressed relative to respective controls, which were given an arbitrary value of 1. The error bars represent the standard errors.

Figure 5:
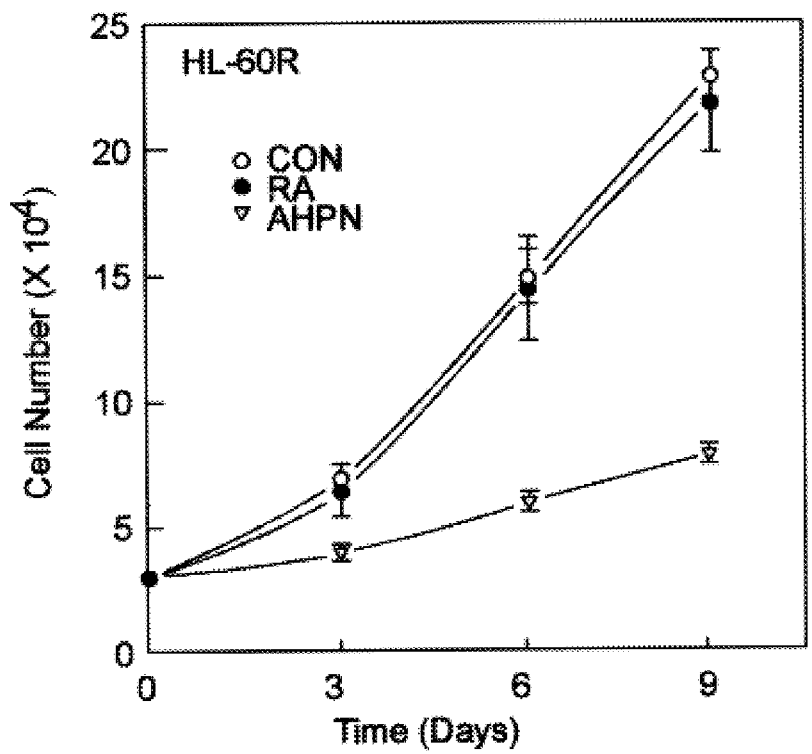

FIG. 5 shows AHPN-mediated inhibition of HL-60R proliferation. HL-60R cells were seeded at cell concentrations of $3 \times 10^4$ cells per well in DMEM:F-12 supplemented with 5% FBS. AHPN or RA was added to a final concentration of 1 μM and medium and supplements were changed every 2 days. Cell counts were performed utilizing a hemocytometer. The results represent the mean ±SEM of three independent experiments.

Figure 6:
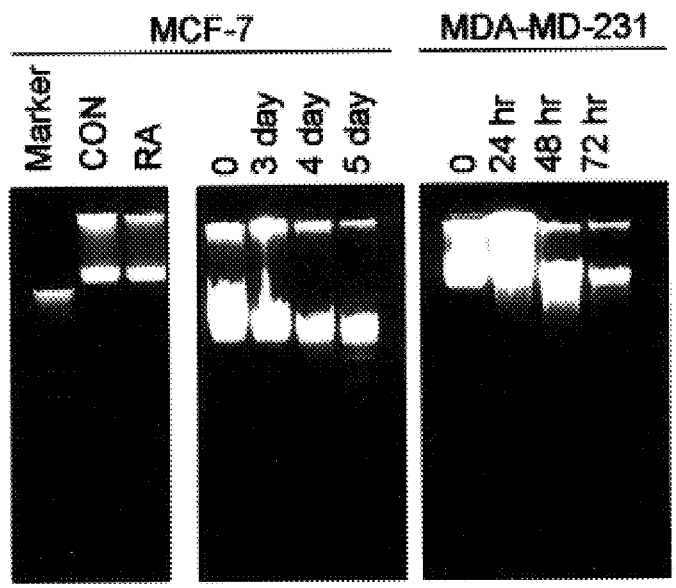
Figure 7A:
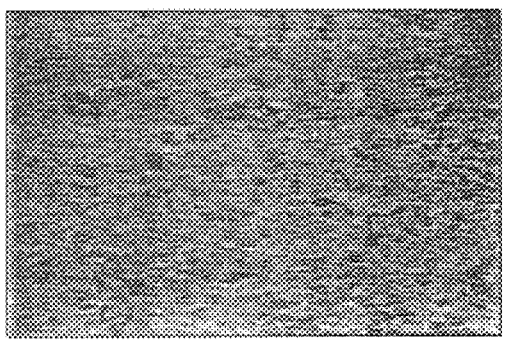
Figure 7B:
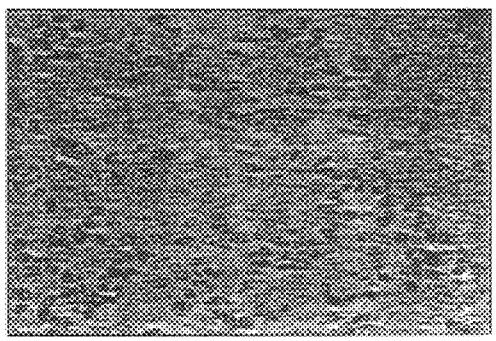
Figure 7C:
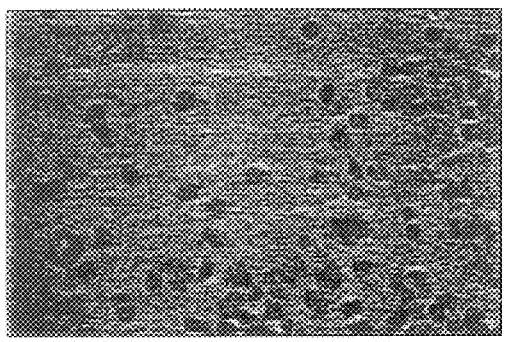
Figure 7D:
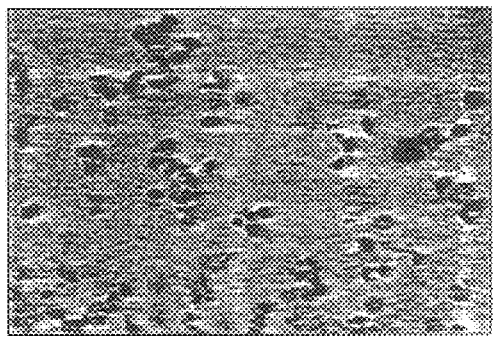
Figure 7E:
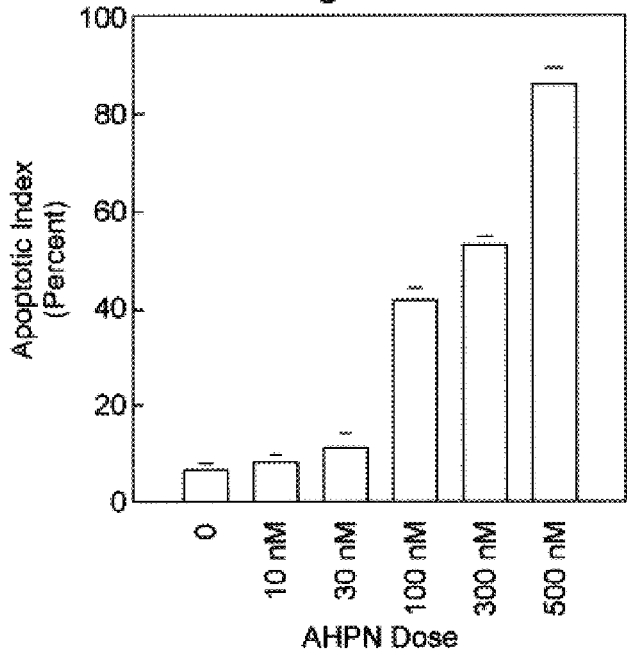

FIG. 6 shows DNA fragmentation induced by AHPN in MCF-7 and MDA-MB-231 cells. MCF-7 and MDA-MB-231 cells were seeded in DMEM:F-12 medium supplemented with 5% FBS and incubated overnight. AHPN or RA were added to final concentrations of 1 μM and the cells incubated for various times. DNA was extracted and fractionated by gel electrophoresis.

FIGS. 7A–7E show the effect of varying concentrations of AHPN on AHPN-mediated apoptosis in MDA-MB-231 cells. MDA-MB-231 cells were seeded in DMEM:F-12 medium supplemented with 5% FBS, incubated overnight and exposed to vehicle alone (FIG. 7A), or 30 nM (FIG. 7B), 100 nM (FIG. 7C), or 500 nM (FIG. 7D) of AHPN for 72 hours (magnification×100). Medium and supplement were changed every 18 hours. Immunoperoxidase staining of cells was effected and the apoptotic index quantified for the different AHPN dosages. These results are contained in FIG. 7E.

Figure 8A:
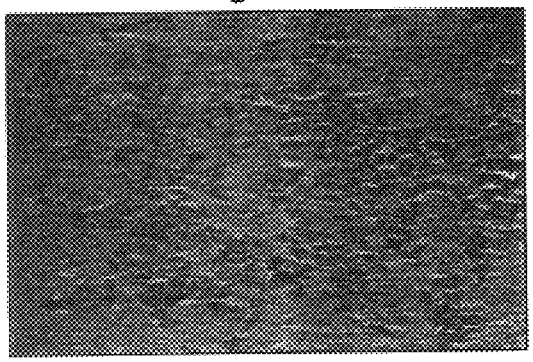
Figure 8B:
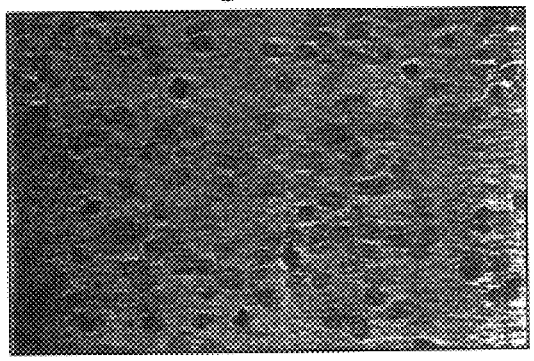
Figure 8C:
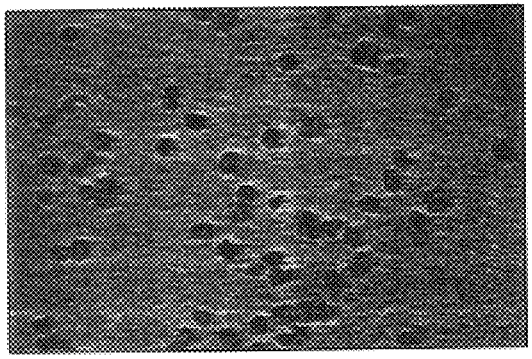
Figure 8D:
Figure 8E:
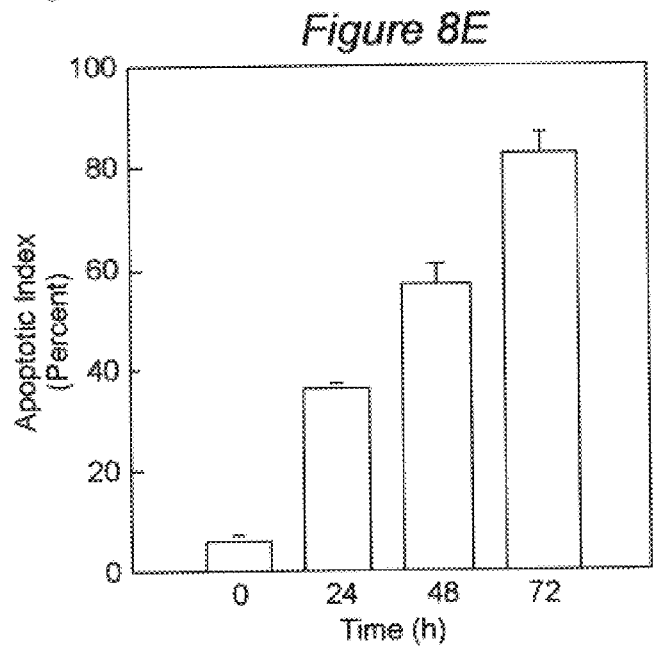

FIGS. 8A–8E show AHPN-mediated apoptosis in MDA-MB-231 cells. MDA-MB-231 cells were seeded in DMEM:F-12 medium supplemented with 5% FBS, incubated overnight and exposed to vehicle alone (FIG. 8A), or 1 μM AHPN for 24 hours (FIG. 8B), 48 hours (FIG. 8C) or 72 hours (FIG. 8D). Immunoperoxidase staining for apoptotic cells was effected (magnification×100). The percent of apoptotic cells was then quantified as a function of length of exposure to AHPN. These results are in FIG. 8E.

Figure 9A:
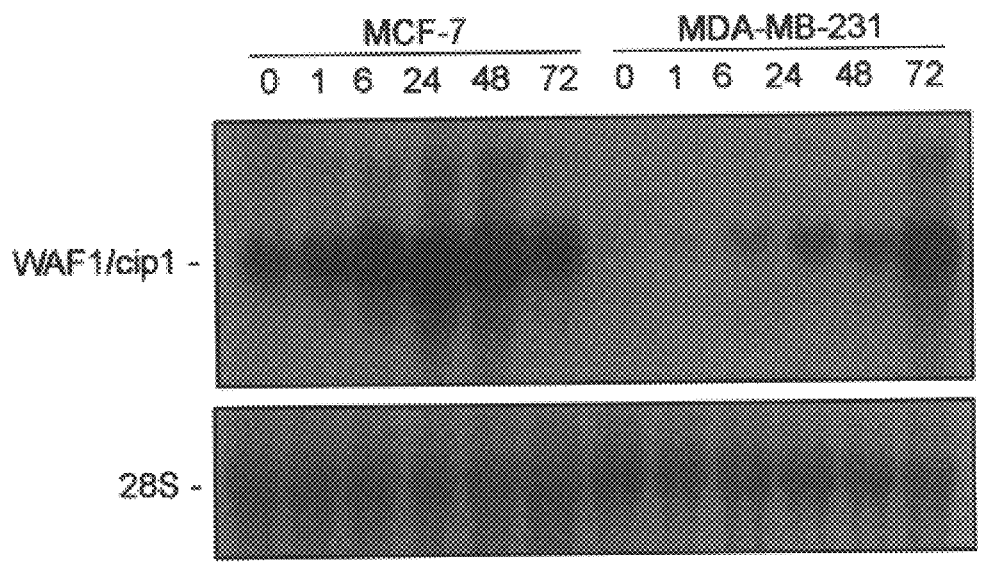
Figure 9B:
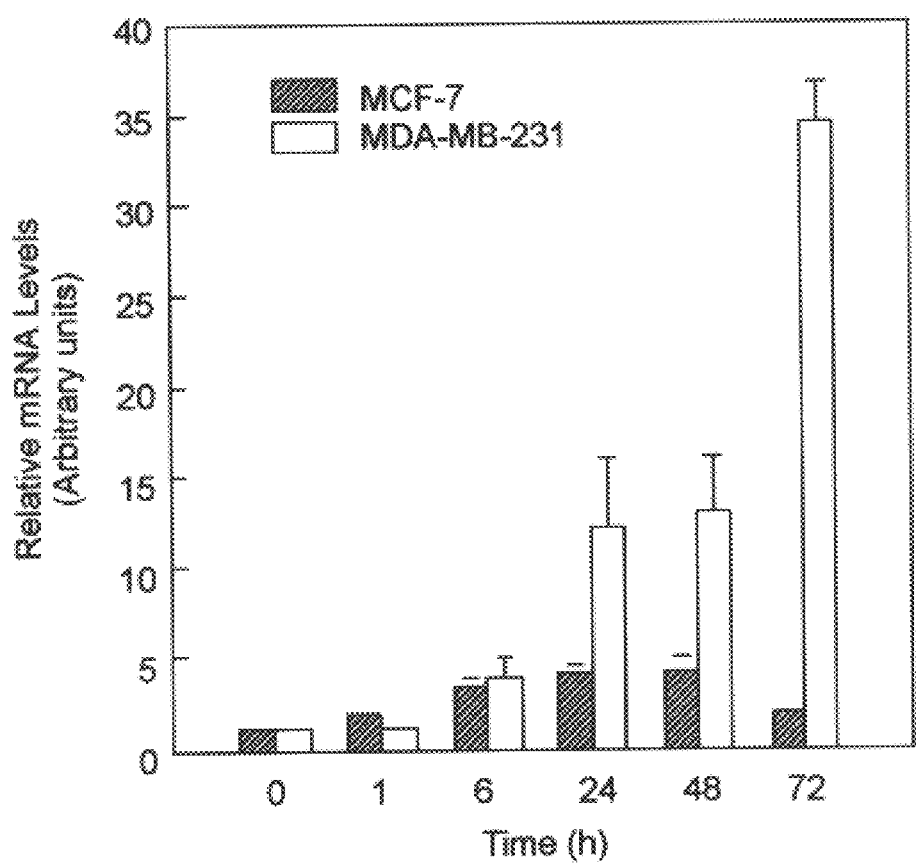

FIGS. 9A–9B show AHPN induction of WAF1/CIP1 mRNA expression in MCF-7 and MDA-MB-231 cells. MCF-7 and MDA-MB-231 cells were incubated in DMEM:F-12 (1:1) supplemented with 5% FBS and AHPN (1 μM) was added at various times during a total incubation period of 72 hours. All cultures were harvested at the end of the 72 hour incubation period. The zero-time culture that was incubated over the 72 hour period in the absence of AHPN served as the control for those cells incubated for various times with AHPN. Total RNA was extracted and Northern blots performed. FIG. 9A shows a representative Northern blot assay. FIG. 9B quantifies the results of two independent experiments. The values are expressed relative to respective controls, which were again given an arbitrary value of 1. The error bars represent the standard errors.

Figure 10:
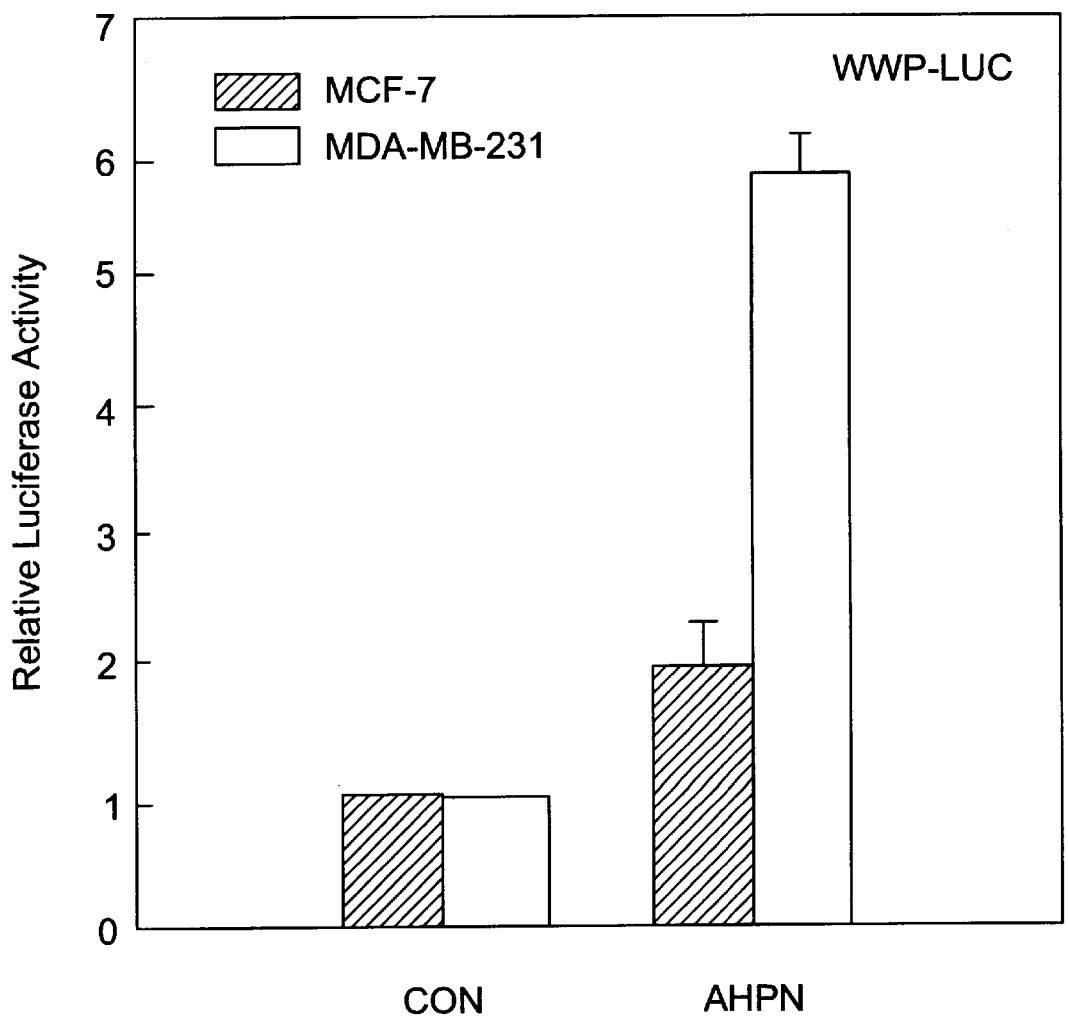

FIG. 10 shows AHPN-enhanced WAF1/CIP1 transcription in MDA-MB-231 and MCF-7 cells. MCF-7 and MDA-MB-231 cells logarithmically growing in 10 cm plates ($3 \times 10^6$ cells/plate) in DMEM:F-12 (1:1) supplemented with 5% FBS were transiently transfected with a WAF1/CIP1 luciferase reporter construct, and luciferase activity then determined.

Figure 11A:
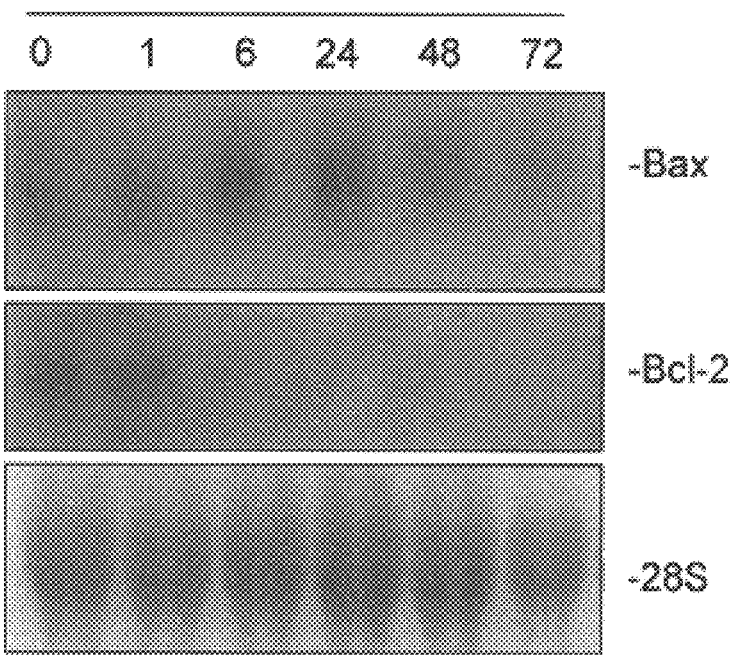
Figure 11B:
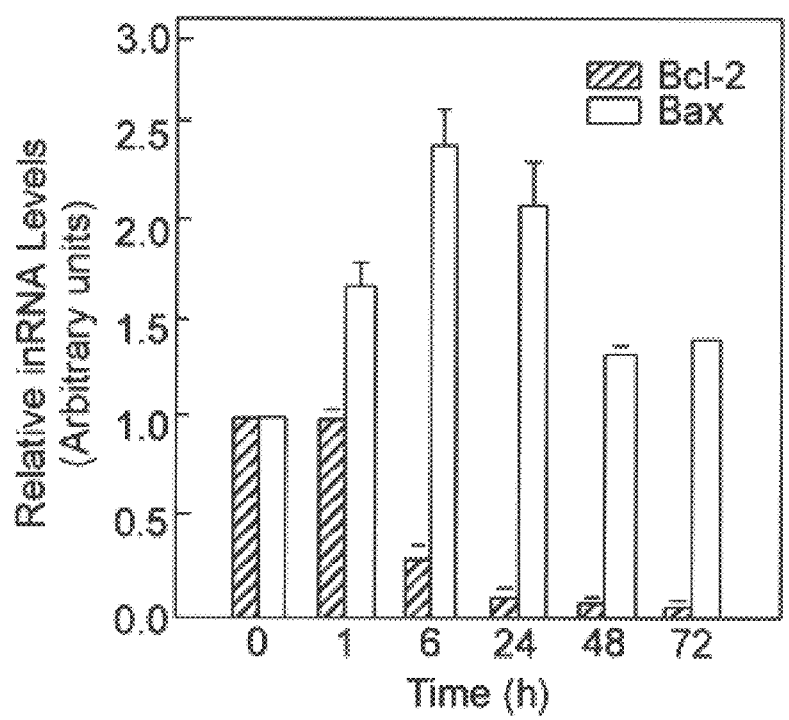

FIGS. 11A and 11B show AHPN modulation of bcl-2 and bax mRNA levels. MCF-7 cells seeded in DMEM:F-12 supplemented with 5k FBS were grown in the presence and absence of 1 μM AHPN for varying amounts of time. Total RNA was extracted and Northern blots performed. FIG. 11A shows a representative Northern blot assay. FIG. 11B quantifies two independent experiments. The values are expressed relative to respective controls, which were again given an arbitrary value of 1. The error bars represent the standard errors.

Figure 12A:
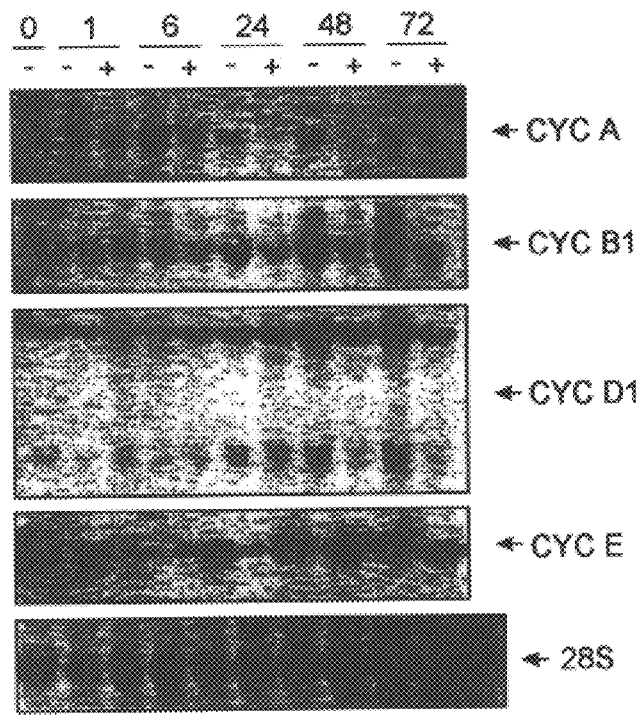
Figure 12B:
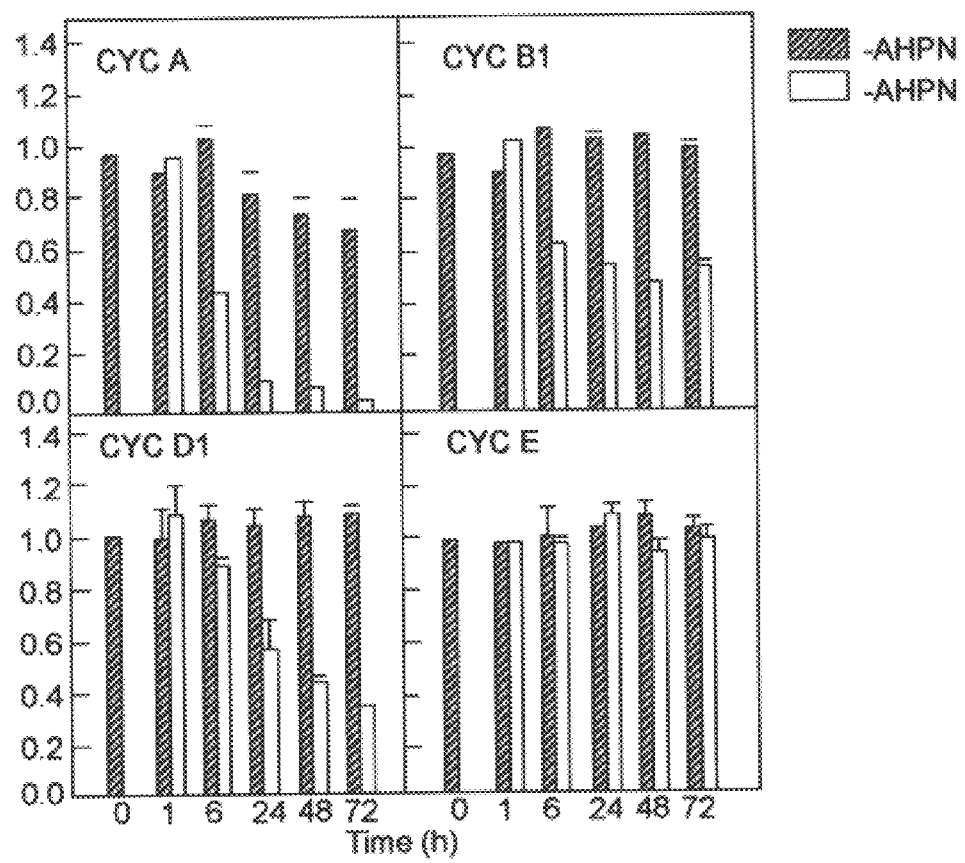

FIGS. 12A and 12B show AHPN modulation of cyclin A, B1, D1 and E on RNA levels. MCF-7 cells seeded in DMEM:F-12 supplemented with 5% FBS were grown in the presence and absence of 1M AHPN for varying amounts of time. Total RNA was extracted and Northern blots performed. FIG. 12A shows a representative Northern blot assay. FIG. 12B is a quantification of two independent experiments. The values are expressed relative to respective controls, which were again given an arbitrary value of 1. The error bars represent the standard errors.

DETAILED DESCRIPTION OF THE INVENTION

The present invention is based on the identification of a synthetic retinoid 6-[3-adamantyl-4-hydroxyphenyl]-2-naphthalene carboxylic acid (APHN) which has been discovered to possess novel properties which render it well suited as an anti-cancer agent, in particular for the treatment or prevention of breast cancer or leukemia. Specifically, it has been discovered that this retinoid mediates $G_0/G_1$ arrest and apoptosis of breast cancer and leukemia cell lines. Thus, 6-[3-adamantyl-4-hydroxyphenyl]-2-naphthalene carboxylic acid (AHPN) provides for the programmed death of cancer cells. This is surprising, because previous retinoids having anticancer activity have typically been cytostatic in their inhibition of cancer cell growth.

Also surprising is the fact that while AHPN selectively transactivates RARγ (Bernard et al, *Biochem. Biophys. Res. Commun.*, 186:977–983 (1992)), this compound apparently mediates $G_0/G_1$ arrest and apoptosis via a mechanism which operates independently of retinoic acid receptor (RAR) and retinoid X receptor (RXR) expression. This is substantiated by the discovery that AHPN induces $G_0/G_1$ arrest and apoptosis in both retinoic acid-sensitive (RA-sensitive) and retinoic acid-resistant (RA-resistant) cancer cell lines.

Further surprising is the fact that AHPN induces $G_0/G_1$ arrest and apoptosis of both estrogen receptor positive (ER+)

and estrogen receptor negative (ER−) cell lines. By contrast, other compounds such as retinoic acid and tamoxifen have been reported only to be active against ER+ breast cancers. This is therapeutically significant, because this allows AHPN to be used for the treatment or prevention of both ER+ and ER− breast cancers.

As noted, the therapeutic activity of AHPN occurs by $G_0/G_1$, arrest and apoptosis. It is known that apoptosis of cancer cells can be triggered through a number of different pathways. (Isaacs et al, *Curr. Opin. Oncol.*, 6:82–89 (1994)). Moreover, a number of different cellular proteins have been reported to enhance or inhibit $G_1$ arrest or programmed cell death. For example, the cellular proteins bcl-2 (Vaux, R. L. *Proc. Natl. Acad. Sci., USA*, 90:786–789 (1993) ) bclX$_L$ (Boise et al, *Cell*, 79:597–608 (1993), Ich-I$_s$ (Wang et al, *Cell*, 78:739–750 (1994)) promote cell survival, while WAFI/CIP1 induces $G_1$ arrest. (Hunter et al, *Cell*, 79:573–582 (1994)), and bcX (Oltvai et al, *Cell*, 74:609–619 (1993)), Ich$_m$ (Wang et al, *Cell*, 78:731–750 (1994)), and TGF/β (Polyak et al, *Genes Dev.*, 8:9–22 (1994)), enhance cell death.

Based on the results of gene expression studies which are discussed in greater detail in the examples which follow, it appears that AHPN induces $G_0/G_1$ arrest and apoptosis via a unique pathway which apparently involves the activation of downstream effectors of p53, but which operates in a p53-independent manner. This is supported by the fact that AHPN has been discovered to markedly enhance WAF1/CIP1 mRNA levels in several breast cancer cell lines (MCF-7 and MDA-MB-231), while significantly decreasing bcl-2 mRNA levels in another breast cancer cell line (MCF-7). Also, AHPN was found to significantly enhance bax mRNA levels by a breast cancer cell line (MCF-7). By contrast, it was found that AHPN apparently does not modulate either TGF-B1 mRNA or protein levels.

Also, it has been discovered that exposure of cultured breast cancer cell lines to AHPN results in significant decreases in mRNA levels of some cyclins, e.g., cyclin D1, cyclin A and cyclin B1. However, when the same cell lines were exposed to AHPN, no effects on cyclin E mRNA levels were observed. This further substantiates the apoptosis inducing activity of AHPN, because cyclins are well known to be important mediators of cell cycle progression (van der Hevvel et al, *Science*, 262:2050–2054 (1993)).

That AHPN induces apoptosis is also substantiated by morphological changes which were found to occur to cancer cell lines which were exposed to AHPN in culture. These changes include marked nuclear fragmentation and chromosome condensation. Moreover, that AHPN induced these morphological changes is substantiated by the fact that such morphological changes were observed to progressively increase as AHPN concentration was increased.

The effects of AHPN on cancer cells, and in particular on breast cancer cells and leukemia cells indicate that this compound may be used for the treatment or prevention of breast cancer or leukemia in subjects in need of such treatment.

In particular, AHPN can be used to treat persons who have been diagnosed to have breast cancer or leukemia, or to prevent cancer in persons who are at elevated risk of developing breast cancer or leukemia. The latter group includes persons with a family history of breast cancer or leukemia, or who have been shown to express markers, e.g., proteins, the expression of which is correlated with an increased incidence of breast cancer or leukemia.

Treatment or prevention of breast cancer or leukemia according to the invention is effected by administering a therapeutically or prophylactically effective amount of AHPN to a subject in need of such treatment or prevention. A therapeutically or prophylactically effective dosage of AHPN will range from about 0.001 mg/kg to 10 mg/kg by body weight, more preferably from 0.01 to 5 mg/kg by body weight and most preferably the dosage will approximate that which is typical for the administration of retinoic acid, which typically ranges from about 2 μg/kg/day to 2 mg/kg/day.

Such administration may be effected in a single or multiple dosages, which typically will be administered daily. However, the dosage regimen may be varied dependent upon the condition of the subject treated, and other factors, such as whether AHPN is administered in conjunction with any other anti-cancer agents or treatments such as radiation therapy. Treatment will typically be effected over a prolonged time period.

The administration of AHPN for the treatment or prevention of breast cancer or leukemia can be effected by any pharmaceutically acceptable route, e.g., orally, intraocularly, parenterally, topically, or via inhalation.

Parenteral administration according to the present invention includes intravenous, intramuscular, subcutaneous, rectal, surgical and intraperitoneal routes of administration as well as the administration of slow or sustained release compositions. Of these, intravenous, intramuscular and subcutaneous routes of administration are generally preferred.

AHPN will be provided in the form of a pharmaceutically acceptable formulation by the addition of one or more acceptable carrier(s) or excipients and optionally by the addition of other active agents, e.g., other anti-cancer agents. The carrier(s) or excipient(s) are acceptable in the sense of being compatible with the other ingredients in the formulation and being safe for pharmaceutical usage. (See, e.g., *Remingtons Pharmaceutical Sciences*, by E. W. Martin (Mack Publ. Co., Eastern Pa.), for a listing of typical pharmaceutically acceptable carriers and excipient and conventional methods of preparing pharmaceutically acceptable formulations.).

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage.

Essentially, these compositions will include, as noted above, a therapeutically or prophylactically effective amount of AHPN in combination with a pharmaceutically acceptable carrier and, in addition, may include other active agents, e.g., other anti-cancer agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., AHPN and optionally pharmaceutical adjuvants in an excipient, such as, for example, water, saline, aqueous dextrose, glycerol, ethanol, or the like, to form a solution or suspension. If desired, the pharmaceutical composition may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Suitable methods for preparing such dosage forms are well known in the art. (See, e.g., *Remington's Pharmaceutical Sciences*, referenced above.).

For oral administration, fine powders or granules may contain diluting, dispersing and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is preferably effected by injection. Injectables can be prepared in conventional forms, either as liquid solutions or suspensions, solid forms suitable for solution or suspension in liquid prior to injection, or as emulsions. Also parenteral administration includes use of a slow release or sustained release system, such that a constant level of dosage is maintained. See e.g., U.S. Pat. No. 3,710,795, which is incorporated by reference herein.

As noted, the subject AHPN formulations may contain other active agents. Such active agents include any compound suitable for the prevention or treatment of cancer, or more specifically the treatment or prevention of breast cancer or leukemia.

For example, the subject AHPN containing formulations may include other retinoids reported to possess anti-cancer activity, e.g., retinoic acid, N-(4-hydroxyphenyl) retinamide (4-HPR), 9-cis-retinoic acid, retinoyl-glucuronide N-glycoside analogs (see, U.S. Pat. No. 5,516,792), or other anti-cancer agents, e.g. methotrexate, anti-estrogens, such as tamoxifen and toremifene, doxorubicin, daunorubicin, adriamyicin, etc. Other active agents which may be incorporated in the subject AHPN formulations include cytokines, e.g., interferons such as gamma, beta or alpha interferon, alpha or beta tumor necrosis factors, interleukins, colony stimulating factors, among others. The incorporation of an interferon in the subject AHPN formulation is potentially advantageous because it has been previously reported that some retinoids exhibit synergistic anti-cancer activity when used in conjunction with an interferon, specifically alpha is interferon or gamma interferon.

Similarly, the incorporation of anti-estrogens, such as tamoxifen or toremifene, in the subject AHPN containing formulations is potentially advantageous because it has been reported that tamoxifen exhibits synergistic breast cancer chemopreventive effects when combined with the retinoid fenretinimide (4-HPR) (Costa, A. *Eur. J. Cancer*, 29A(4):589–592 (1993)).

The following examples illustrate the preparation and use of specific embodiments of the invention, but are in no way intended to limit the scope of the invention.

EXAMPLES

The following materials and methods were used in the examples:

Retinoid Materials

All-trans-RA was obtained from Sigma (St. Louis, Mo.) and 4-[1,5,6,7,8-tetrahydro-5,5,8,8-tetramethyl-2-naphthalenyl) cyclopropyl]benzoic acid (SR11246) was prepared as described by Dawson et al (In *Retinoids: New Trends in Research and Clinical Applications*, Livrea, M. A. and Packer, L. (eds.), Marcel Dekker: New York, pp. 205–221 (1992)). The synthesis of 6-[3-[1-adamantyl]-4-hydroxyphenyl]-2-naphthalene carboxylic acid (AHPN) is described in U.S. Pat. No. 4,717,720 (see Example 13).

Supplies

Dulbecco's modified Eagle's medium, Ham's F-12 medium and fetal bovine serum (FBS) were obtained from Gibco-BRL (Grand Island, N.Y.). Dulbecco's modified Eagle's medium (Phenol red-free) was purchased from Biofluids (Rockville, Md.). HEPES, tamoxifen, and charcoal limpet sulfatase, were obtained from Sigma Chemicals (St. Louis, Mo.). [$^{14}$C]chloramphenicol (53 mCi mmol$^{-1}$) and [$^{32}$P]αdCTP (3000 Ci mmol$^{-1}$) was supplied by Amersham (Arlington Heights, Ill.).

Cell lines and culture

The MCF-7, T47D and MDA-MB-231 cell lines were a kind gift of Dr. Marc Lippman (Lombardi Cancer Center, Washington, D.C.). The MDA-MB-468 cells were provided by Dr. Anne Hamburger (University of Maryland Cancer Center, Baltimore, Md.). Cells were maintained in Dulbecco's modified Eagle's (DMEM): Ham's F-12 medium, supplemented with 5% FBS as previously reported (Fontana, J. A., *Exp. Cell Res.*, 55:136–144 (1987)).

Growth experiments

Cells were plated in DMEM:F-12 (1:1) medium supplemented with FBS for 24 h. MCF-7 cells were plated at an initial cell concentration of $3 \times 10^4$ cells per well, while T47D, MDA-MB-231 and MDA-MB-468 were plated at a cell concentration of $1 \times 10^4$ cells per well. The treatment with RA or AHPN was for 3, 6, or 9 days in the same medium. The medium and retinoids were changed every 2 days. The retinoids were dissolved in dimethyl sulfoxide (DMSO). The final concentration of DMSO in all the cultures was 0.1%; control cells were incubated with DMSO at the same final concentration.

Plasmid constructs, transient transfection and CAT assay

The $\beta_2$-RARE-tk-CAT and the CRBP II-tk CAT and APO-l-tk CAT reporter plasmids, which were kindly provided by Dr. X-k Zhang of the La Jolla Cancer Center (La Jolla, Calif.), carry the RARE and RXRE, respectively, upstream of the thymidine kinase (tk) promoter containing the CAT gene. Variations in transfection efficiencies were adjusted by using the plasmid pRSV2 (MacGregor et al, *Somat. Cell Mol. Genet.*, 13:253–265 (1987)), which carries an *Escherichia coli* lac Z gene under the control of a Rous sarcoma virus long terminal repeat and encodes the β-galactosidase enzyme. The (AP-1)$_3$-tk-CAT reporter construct was obtained from Dr. Ronald Evans (La Jolla, Calif.). WWP-Luc carries a 2.4 kb 5'-proximal region of the WAF1/CIP1 gene fused to a promoterless luciferase reporter gene (El-Deiry et al, *Cell*, 75:817–825 (1993)).

cDNA probes

The full-length human WAF1 cDNA probe was kindly provided by Drs. Kinzler and Vogelstein (Johns Hopkins University, Baltimore, Md.). The human cyclin D1 and E cDNA probes (Xiong et al, *Cell*, 65:691–699 (1991), and Xiong et al, *Genomics*, 13:575–584 (1992)) were obtained from Dr. David Beach (Howard Hughes, Cold Spring Harbor Laboratory, NY). The human cyclin A and B1 cDNA probes (Pines et al, *Cell*, 58:833–846 (1989); and Pines et al, *Nature*, 346:760–763 (1990)), were a gift of Dr. Tony Hunter (The Salk Institute, San Diego, Calif.). Probes were labelled according to the random primer method of Feinberg et al, (*Anal. Biochem.*, 132:6–13 (1983)).

Transient transfections, CAT and luciferase assays

Transient transfections were performed as previously described (Sheikh et al, *J. Cell. Biochem.*, 53:393–404 (1993)). Cells were plated in a 10 cm plate at a density of 3×10$^6$ cells per plate. The medium was changed 2 h before transfection. The cells were co-transfected with various plasmids and the total amount of DNA was corrected to 20 µg per plate by adding plasmid pUC19. MDA-MB-231 and MCF-7 cells were shocked with 20% glycerol for 7 min and 2 min, respectively, 6 h following the addition of DNA. Fresh medium was added following washing the cells with 1× PBS. The cells were harvested 48 h after the transfection. For CAT assays, the cells were trypsinized and resuspended in 100 µl 0.25 M Tris-HCl, pH 8.0. After three cycles of freezing and thawing, cell lysates were collected and CAT assays performed as previously described (Sheikh et al, *J. Cell. Biochem.*, 53:393–404 (1993)).

For luciferase assays, the cells were washed with PBS, and 300–400 µl of lysis buffer (25 mM glycylglycine pH 7.8, 1.5 mM MgSO4 a, 4 mM EGTA, 100 mM DTT and 1% Triton X-100) added to the cells and the cell harvested. The lysates were centrifuged for 5 min in a microcentrifuge. The supernatants were supplemented with 12 mM K$_2$HPO$_4$ and 1.6 mM ATP and assayed for luciferase activity by measuring light units in a standard luminometer for 10 s. Relative light units were corrected with respect to β-galactosidase activity.

Northern blots

Total RNA was extracted and 20 µg of total RNA was loaded in agarose gel and Northern blot analysis were performed essentially as previously described (Sheikh et al, *Biophys. Res. Commun.*, 183:1003–1010 (1992)).

Analysis of cell cycle phase distribution

Flow cytometric analysis DNA content was performed to assess the cell cycle phase distribution as described previously (Sheikh et al, *Anticancer Res.*, 13:1387–1392 (1993)). AHPN (1 µM) was added to logarithmically growing MCF-7 or MDA-MB-231 cells. Cells were harvested by trypsinization at various times and stained for DNA content using propidium iodide fluorescence as previously described (Sheikh et al, *Anticancer Res.*, 13:1387–1392 (1993)). The computer program Multicycle from Phenix Flow Systems (San Diego, Calif.) was used to generate histograms, which were used to determine the cell cycle phase distribution.

Apoptosis Assay

Apoptosis was detected by labelling the 3'OH ends of DNA utilizing digoxigenin incorporation by terminal deoxynucleootidyltransferase. Antidigoxigenin antibodies and immunoperoxidase staining were utilized to demonstrate digoxigenin-nucleotide incorporation by utilizing the Apotag detection system (Oncor, Gaithersburg, Md.). In brief, cells were spun onto microscope slides, rinsed with PBS and finally incubated in a reaction mixture containing terminal transferase and digoxigenin dUTP at 37° C. for 1 h. The specimens were then washed, antidigoxigenin antibody coupled to horseradish peroxidase was then added, and the cells were incubated for 30 min at room temperature. Following the rinsing with PBS, diaminobenzidine tetrachloride (DAKO, Carpenteria, Calif.) was added and the cells incubated for 10 min. The percent peroxidase positive cells were determined by counting 200 cells in random fields in two separate experiments.

Example 1

AHPN inhibition of breast carcinoma proliferation

Numerous investigators have demonstrated that estrogen receptor (ER)-positive breast carcinoma cells are sensitive to the antiproliferative effects of RA while ER-negative cells are refractory (Roman et al, *Cancer Res.*, 53:5940–5945 (1993); Sheikh et al, *J. Cell. Biochem.*, 53:393–404 (1993); and van der Burg et al, *Mol. Cell. Endo.*, 91:149–157 (1993)). Therefore, in order to determine whether AHPN displays the same spectrum of antiproliferative activity against breast carcinoma cells as RA, the ability of AHPN to inhibit the proliferation of both ER-positive and ER-negative breast carcinoma cells was investigated. The results in FIG. 1 show that AHPN significantly inhibited the proliferation of both the RA-sensitive, ER-positive MCF-7 and T47D, as well as the RA-refractory, ER-negative, MDA-MB-231 and MDA-MB-468 human breast carcinoma cell lines (HBC). In addition, AHPN displayed significantly greater antiproliferative activity against MCF-7 and T47D cells than that noted with RA (data not shown). The concentration of AHPN required for 50% inhibition of growth (IC$_{50}$) was 300 nM and 150 nM for MCF-7 and MDA-MB-231 cells, respectively (see FIG. 2). By contrast, RA did not inhibit the growth of MDA-MB-231 or MDA-MB-468 cells and displayed an IC$_{50}$ of 100 nM when tested against MCF-7 and T47D cells (Sheikh et al, *J. Biol. Chem.*, 269:21440–21447 (1994)). Also, it was discovered that AHPN arrested MCF-7 and MDA-MB-231 cells in the G$_0$/G$_1$ phase (FIGS. 3A and 3B). Exposure of both these cell lines to AHPN resulted in a significant increase in cells in G$_0$/G$_1$, accompanied by a decrease in the percent of cells in G2+M and S phase. RA had no effect on the cell cycle phase distribution of MDA-MB-231 cells (data not shown).

Example 2

AHPN binding and activation of endogenous retinoid receptors

AHPN has been reported as RARγ-selective in both retinoid receptor binding and transcriptional activation assays (Bernard et al, *Biochem. Biophys. Res. Commun.*, 186:977–983 (1992)). Tritiated 6-(5,6,7,8-tetrahydro-5,5,8,8-tetramethyl-2-anthracenyl)benzoic acid gave K$_d$ values for RARα and RARβ that were higher by 32-fold and 84-fold, respectively, than for the RARγ. Transcriptional activation assays in HeLa cells using expression vectors for the receptors and the (TRE)$_3$-tk-CAT reporter plasmid required AHPN concentrations for 50% maximal activation that were 19-fold and 3.9-fold higher for RARα and RARβ, respectively than for RARγ (Bernard et al, *Biochem. Biophys. Res. Commun.*, 186:977–983 (1992)).

The present inventors theorized that if AHPN-mediated inhibition of breast carcinoma proliferation occurred through activation of RARγ, similar or greater transactivation of a transfected RARE-mediated reporter gene with AHPN than that found with RA, in MDA-MB-231 cells, which only possesses RARγ and are refractory to the antiproliferative effects of RA (Roman et al, *Cancer Res.*, 53:5940–5945 (1993); Sheikh et al, *J. Cell. Biochem.*, 53:393–404 (1993); and van der Burg et al, *Mol. Cell. Endo.*, 91:149–157 (1993)) would be expected to be seen. Therefore, the ability of AHPN to activate the RARE pathway in MCF-7 and MDA-MB-231 cells was compared utilizing a β$_2$-RARE-controlled CAT reporter gene. The β$_2$-RARE is predominantly activated by RAR/RXR heterodimers and to a lesser extent by RXR homodimers and has a direct repeat 5 (DR5) -type response element located in the promoter region of the RARβ$_2$ gene (Zhang, *Nature*, 355:441–446 (1992); and Zhang et al, *Mol. Cell. Biol.*, 14:4311–4323 (1994)). As shown in FIG. 4, AHPN displayed significantly decreased potency than RA in its ability to transactivate the endogenous retinoid receptors in both MCF-7 and MDA-MB-231 cells.

Based on these results, it was concluded that AHPN apparently does not mediate its antiproliferative effects through the RAR pathway since AHPN is a much more potent inhibitor of MCF-7 and MDA-MB-231 growth than RA but displays markedly less transactivation of the $\beta_2$RARE response element than RA in both cell types. HL-60R cells do not possess a functional RAR and their growth is not inhibited by RA (Robertson et al, *Blood*, 80:1885–1889 (1982)). The effect of AHPN on HL-60R growth was also studied to further assess the role of the RAR pathway on AHPN-mediated inhibition of growth. AHPN was found to markedly inhibit the proliferation of HL-60R leukemia cells while RA had no effect (FIG. 5). These results further substantiate that the RAR pathway is not involved in AHPN-mediated growth inhibition.

In order to investigate whether AHPN functions through the RXR homodimer selective pathway, the ability of AHPN to transactivate two naturally occurring RXREs, i.e. APO-AI and CRBPII which were transfected into MCF-7 and MDA-MB-231 was compared. The APO-AI, which is activated by RXR/RXR homodimers and to a lesser extent by RAR/RXR heterodimers, is a DR-2 type response element located in the promoter region of the APO-AI gene (Zhang et al, *Nature*, 358:587–597 (1992); and Zhang et al, *Mol. Cell. Biol.*, 14:4311–4323 (1994)). The CRBPII RXRE is activated by RXR/RXR homodimers and is a DR-1-type retinoid response element. SR11246 which induces RXR homodimer formation, was a good activator of the RXRE pathway, while minimal activation of the RXRE was noted in the presence of AHPN (FIG. 4).

Example 3

AHPN modulation of AP-1 activity

Activation of AP-1 mediated gene transcription is closely associated with cellular proliferation (Pardee, *Science*, 246:603–606 (1989)). RA through its RAR and RXR nuclear receptors can antagonize c-Fos/c-Jun-mediated activation of the AP-1 consensus sequence (Schule et al, *Proc. Natl. Acad. Sci. USA*, 88:6092–6096 (1991); Busam et al, *J. Biol. Chem.*, 267:19971–19977 (1992); Jaffey et al, *Cancer Res.*, 52:2384–2388 (1992); and Salbert et al, *Mol. Endocrinol.*, 7:1347–1356 (1993)). Therefore, the effect of AHPN on AP-1-mediated CAT activity was studied in both MCF-7 and MDA-MB-231 cells. As shown in FIG. 4, 1 $\mu$M RA significantly inhibited AP-1-mediated CAT activity in MCF-7 cells, whereas AHPN had no effect. Neither RA nor AHPN modulated AP-1-mediated CAT activity in MDA-MB-231 cells.

Example 4

AHPN-mediated apoptosis

The decrease in MDA-MB-231 and MCF-7 cell counts (FIG. 1), and change in cell appearance following exposure to AHPN, but not to RA, suggested that exposure to APHN resulted in programmed cell death, i.e., apoptosis. To further investigate this possibility, cell morphology was examined and DNA electrophoretic analysis was performed on MDA-MB-231 and MCF-7 cells following exposure to 1 $\mu$M RA or 1 $\mu$M AHPN. Following exposure to AHPN, MCF-7 cells demonstrated morphologic changes associated with the apoptotic process (Isaacs, J. T., *Curr. Opinion in Oncol.*, 6:82–89 (1994)). The cells had marked nuclear fragmentation and chromatin condensation with the nuclear and cytoplasmic membranes remaining intact (data not shown). No such changes were found in MCF-7 cells following exposure to RA. Incubation of MDA-MB-231 or MCF-7 cells with 1 $\mu$M AHPN resulted in internucleosomal cleavage and laddering of the DNA on gel electrophoresis (FIG. 6), indicative of apoptosis (Isaacs, J. T., *Curr. Opinion in Oncol.*, 6:82–89 (1994)). Internucleosomal cleavage and DNA laddering was not seen following exposure of MCF-7 or MDA-MB-231 cells to RA (FIG. 6).

AHPN-mediated apoptosis was also evaluated in MDA-MB-231 cells utilizing the Apotag assay in which 3'OH ends of the DNA breaks associated with apoptosis are labeled with digoxigenin-coupled dUTP using terminal deoxynucleotidyl transferase and digoxigenin detected using immunoperoxidase staining. As shown in FIG. 7, increasing AHPN concentrations resulted in a progressive increase in the percent of apoptotic cells as indicated by fragmentation of the DNA and nuclear immunoperoxidase staining. Also, exposure to 1 $\mu$M AHPN for varying periods of time (0, 24, 48 of 72 h) resulted in a progressive increase in the percent of apoptotic cells (FIG. 8). Exposure to 1 $\mu$M RA for 72 h resulted in 8% of MCF-7 cells displaying digoxigenin UTP incorporation while no staining was seen in MDA-MB-231 cells (data not shown).

Example 5

AHPN induction of WAF1/CIP1

Apoptosis can be triggered in cells through a variety of pathways (Isaacs, J. T., *Curr. Opinion in Oncol.*, 6:82–89 (1994)). A number of cellular proteins either enhance or inhibit $G_1$ arrest or programmed cell death. The cellular proteins bcl-2 (Vaux, *Proc. Natl. Acad. Sci. USA*, 90:786–789 (1993)), bclX$_L$ (Boise et al, *Cell*, 74:597–608 (1993), Ich-1s (Wang et al, *Cell*, 78:739–750 (1994)) promote cell survival, while WAF1/CIP1 induces $G_1$ arrest (Hunter et al, *Cell*, 79:573–582 (1994)), and bax (Oltvai et al, *Cell*, 74:609–619 (1993)), Ich$_L$ (Wang et al, *Cell*, 78:739–750 (1994), and TGF-$\beta$1 (Polyak et al, *Genes Dev.*, 8:9–22 (1994)) enhance cell death. Therefore, the ability of AHPN to modulate WA1/CIP1, bax, TGF-$\beta$1 and bcl-2 mRNA levels was evaluated.

As shown in FIG. 9, 1 $\mu$m AHPN markedly enhanced WAF1/CIP1 mRNA levels in both MCF-7 cells and MDA-MB-231 cells. AHPN elevated WAF1/CIP1 mRNA levels as early as 1 h after addition to MDA-MB-231 cells, and within 6 h after addition to MCF-7 cells (FIG. 9). There was a six-fold and 35-fold increase in WAF1/CIP1 mRNA levels after 72 h incubation with AHPN in MCF-7 and MDA-MB-231 cells respectively. MDA-MB-231 cells expressed significantly lower WAF1/CIP1 mRNA levels than MCF-7 cells due to the presence of a mutated (nonfunctional) p53, as previously demonstrated (Sheikh et al, *Oncogene*, 9:3407–3415 (1994)). RA did not modulate WAF1/CIP1 mRNA levels (data not shown) in either cell type. That AHPN enhanced WAF1/CIP1 gene transcription may be seen from the results contained in FIG. 10. A six-fold and two-fold increase in luciferase activity in MDA-MB-231 and MCF-7 cells, respectively, was observed when a WAF-luc reporter construct was transfected into the cells in the presence of AHPN.

Example 6

AHPN modulation of bcl-2 and bax mRNA expression

Negative and positive regulators of apoptosis have been identified. Bcl-2 expression enhances cell survival and blocks TGF$\beta$1 induced cell death while bax promotes cell death and may enhance p53-mediated apoptosis. (Selvakumaran et al, *Oncogene*, 9:1791–1798 (1994)). Accordingly, the effect of AHPN on bcl-2 and bax mRNA expression was examined. These results indicated that while AHPN significantly enhanced WAF1/CIP1 mRNA levels in MCF-7 cells within 6 h, it significantly decreased bcl-2 mRNA levels (FIG. 11). Bcl-2 MRNA expression could not be detected in MDA-MB-231 cells in the absence or presence of AHPN. Similarly, AHPN (1 μM) significantly elevated bax mRNA levels within 6 h in MCF-7 cells, while bax mRNA expression could not be detected in MDA-MB-231 cells. Also, it was found that AHPN (1 μM) did not modulate TGFβ1 mRNA or protein levels in either MCF-7 or MDA-MB-231 cells (data not shown).

Example 7

AHPN modulation of cyclin expression

Cyclins are important mediators of cell cycle progression (van der Hevvel et al, *Science*, 262:2050–2054 (1994)). In addition, numerous investigators have suggested that cyclin D1 and cyclin E are rate-limiting for progression through $G_1$ (Jiang et al, *Oncogene*, 8:3447–3457 (1993); Quelle et al, *Genes Dev.*, 7:1559–1571 (1993); and Baldin et al, *Genes Dev.*, 7:812–821 (1994)). Since exposure to AHPN resulted in $G_0/G_1$ arrest, the effect of AHPN treatment on cyclin E, D1, A and B1 expression in MCF-7 cells was examined. As shown in FIG. 12, cyclin D1 mRNA levels were significantly decreased within 6 h of exposure to AHPN. Decreases in cyclin A and cyclin B1 mRNA were also noted within 6 h following the addition of AHPN, while there was no modulation of cyclin E mRNA levels (FIG. 12).

Conclusions

Based on these results, it was concluded that while AHPN displays enhanced binding to and transactivation of the RARγ receptor, AHPN apparently also functions through a RAR and RXR-independent mechanism. Also, AHPN was found to significantly inhibit the proliferation of both ER-positive MCF-7 and T47D cells, as well as ER-negative MDA-MB-231 and MDA-MB-468 cells, whereas RA inhibited only ER-positive breast carcinoma cell proliferation. Moreover, in MDA-MB-231 cells, AHPN was found to display significantly less transactivation than RA of the RAR receptor on the RARl2 RARE as well as the is APO-1 RXRE, which can also be activated by RAR-RXR heterodimers. These results indicate there to be no correlation between AHPN transactivation of the RARγ receptor and its ability to inhibit breast carcinoma cell proliferation, even in MDA-MB-231 cells which only possess a functional RARγ receptor. Also, the results indicate that AHPN does not activate the RXRE pathway (as demonstrated by the lack of CAT activity on transfection of MCF-7 and MDA-MB-231 cells with the CRBPII and APO-1 RXRE-tk-CAT reporter constructs in the presence of AHPN).

Further, AHPN was found to inhibit the proliferation of the RA-resistant HL-60R cells which possess a defective RARγ due to a point mutation in the RARγ gene resulting in its truncation and inability to bind RA. (Robertson et al, *Blood*, 80:1885–1889 (1982)). HL-60R cells do not possess a RARβ or RARγ receptor (Nervi et al, *Proc. Natl. Acad. Sci. USA*, 86:5854–5858 (1989)). Accordingly, these results indicate that growth inhibition by AHPN is not mediated via the RAR pathway in these cells.

As opposed to the cytostatic effect noted with RA in breast cancer cells (Fontana, J. A., *Exp. Cell Res.*, 55:136–144 (1987)), these results indicate that exposure to AHPN results in apoptosis. That AHPN induces apoptosis was demonstrated by several lines of evidence. For example, AHPN treatment of MCF-7 and MDA-MB-231 cells resulted in chromatin condensation and DNA fragmentation while the nuclear and plasma membranes remained intact. These findings are consistent with the process of apoptosis, as opposed to cellular necrosis where there is increased plasma membrane permeability accompanied by cellular edema and osmotic lysis of the cell (Isaacs, J. T., *Curr. Opinion in Oncol.*, 6:82–89 (1994)).

Also, AHPN arrested MCF-7 and MDA-MB-231 cells in the $G_0/G_1$ phase of the cell cycle. This arrest in $G_0/G_1$ was preceded by the marked increased transcription of WAF1/CIP1 mRNA. WAF1/CIP1 inhibits the function of a number of cyclin/cyclin-dependent protein kinase (CDK) complexes including cyclin A-CDK2, cyclin E-CDK2 and cyclin D-CDK-resulting in the arrest of the cells in $G_1$ (Hunter et al, *Cell*, 79:573–582 (1994)). p53-mediated $G_1$ arrest in response to DNA damage appears to require the elevation of WAF1/CIP1 levels (Hunter et al, *Cell*, 79:573–582 (1994)).

The WAF1/CIP1 promoter has a p53 consensus sequence and thus the post-transcriptional elevation of p53 levels following DNA damage results in enhanced WAF1/CIP1 gene transcription and subsequent $G_1$ arrest. It has previously been shown that MCF-7 cells possess a wild-type (functional) p53 while MDA-MB-231 cells possess a mutant (nonfunctional) p53 (Sheikh et al, *Oncogene*, 9:3407–3415 (1994)). Niewolik et al (*Oncogene*, 10:881–890 (1995)) have also reported that p53 derived from MDA-MB-231 cells does not bind to the p53 consensus sequence. Thus, the AHPN-mediated increase in WAF1/CIP1 transcription in MDA-MB-231 and presumably MCF-7 cells must occur through a p53-independent mechanism. It has previously been reported that DNA-damaging agents, as well as serum starvation-induced growth arrest, did not increase p53 levels but did increase WAF1/CIP1 mRNA levels in cells carrying mutant p53 (Sheikh et al, *Oncogene*, 9:3407–3415 (1994)). Incubation with AHPN did not result in elevated p53 levels in either MCF-7 or MDA-MB-231 cells (data not shown). Several investigators have demonstrated that RA-mediated differentiation of HL-60 cells is associated with a p53 independent elevation of WAF1/CIP1 levels (Jiang et al, *Oncogene*, 9:3397–3406 (1994); and Steinman et al, *Oncogene*, 9:3389–3396 (1994)). Michiel et al (*Cancer Res.*, 54:3391–3395 (1994)) have hypothesized the existence of two separate pathways for the induction of WAF1/CIP1, a mitogen-activated p53-independent mechanism and a DNA damage-activated, p53-dependent mechanism. In addition to elevating WAF1/CIP1 levels and inhibiting cyclin/cyclin-dependent protein kinase activity, AHPN significantly decreased cyclin D1, A and B mRNA levels, perhaps also contributing to $G_1$ arrest.

The bcl-2 oncoprotein is found in the inner mitochondrial membrane, as well as other subcellular compartments, i.e., the endoplasmic reticulum and the nuclear membrane (Oltvai et al, *Cell*, 74:609–619 (1993)), where its overexpression results in prolongation of cell survival (Hockenberry et al, *Proc. Natl. Acad. Sci. USA*, 88:6961–6965 (1991)). Bcl-2 is reported to both homodimerize and heterodimerize with a number of other proteins, including bax, bcl $X_L$, bcl $X_S$, and Mcl-1 (Sato et al, *Proc. Natl. Acad. Sci. USA*, 91:9238–9242 (1994)). Heterodimer formation with bcl $X_S$, or bax, as well as homodimer formation by bax, inactivates bcl-2. Selvakumaran et al, *Oncogene*, 9:1791–1798 (1994) and Miyashita et al, *Oncogene*, 9:1799–1805 (1994) have reported that the elevation in p53 leads to the upregulation of bax and the downregulation of bcl-2 levels. These observations suggest that p53 markedly inhibits bcl-2 MRNA expression, while elevating the levels of bax MRNA levels. Interestingly, bcl-2 is also down-regulated by mutant p53 (Haldar et al, *Cancer Res.*, 54:2095–2097 (1994) and Zhan et al, *Oncogene*, 9:3743–3751 (1994)) have speculated that elevation of bax and down regulation of bcl-2 play major roles in irradiation-induced apoptosis. AHPN-mediated elevation of bax mRNA levels and downregulation of bcl-2 mRNA occurred in MCF-7 cells, which possess a wild-type p53. Bcl-2 or bax mRNA expression in MDA-MB-231 cells were not detected in the previously described experiments. By contrast, Haldar et al, *Cancer Res.*, 54:2095–2097 (1994), detected low bcl-2 protein levels in MDA-MB-231 cells. This discrepancy may be attributable to different strains of MDA-MB-231. The results also indicate that MDA-MB-231 cells are exquisitely sensitive to AHPN-mediated $G_0/G_1$ arrest and programmed-cell death. It is possible that the low levels of bcl-2 may enhance the sensitivity of MDA-MB-231 to this retinoid.

Moreover, the foregoing results show that AHPN displays a wide spectrum of action by inhibiting the growth of both ER-positive and ER-negative breast carcinoma cell lines. In addition, as opposed to other retinoids, exposure to AHPN results in programmed death of breast carcinoma and leukemia cells. Thus, based on these results, AHPN is well suited for the treatment or prevention of breast cancer or leukemia.

While the invention has been described and illustrated with respect to specific embodiments and features, it will be appreciated that various changes and modifications, can be made without departing from the invention.

What is claimed is:

1. A method of treating or preventing leukemia in a subject in need of such treatment or prevention comprising administering a therapeutically or prophylactically effective amount of 6-[3-[1-adamantyl]-4-hydroxyphenyl]-2-naphthalene carboxylic acid (AHPN).

2. The method claim 1, wherein the leukemia is one characterized by cancer cells which do not express functional retinoic acid receptors (RARs).

3. The method of claim 1, wherein the dosage of AHPN ranges from about 0.001 mg/kg to about 10 mg/kg body weight.

4. The method of claim 1, wherein the daily dosage of AHPN ranges from about 2 µg/kg to about 2 mg/kg body weight.

* * * * *